US012779179B2

(12) United States Patent
Blum et al.

(10) Patent No.: US 12,779,179 B2
(45) Date of Patent: Nov. 3, 2026

(54) CATHETER ARRANGEMENT FOR USE IN PERIPHERAL REGIONAL ANAESTHESIA

(71) Applicant: B. Braun Melsungen AG, Melsungen (DE)

(72) Inventors: Iris Blum, Fuldabrueck (DE); André Weiss, Guxhagen (DE); Nicky Bode, Schimberg (DE); Jacqueline Felmeden, Melsungen (DE)

(73) Assignee: Braun Melsungen AG, Melsungen (DE)

( * ) Notice: Subject to any disclaimer, the term of this patent is extended or adjusted under 35 U.S.C. 154(b) by 658 days.

(21) Appl. No.: 18/317,222

(22) Filed: May 15, 2023

(65) Prior Publication Data

US 2023/0372679 A1 Nov. 23, 2023

(30) Foreign Application Priority Data

May 23, 2022 (DE) ..................... 10 2022 205 130.0

(51) Int. Cl.
*A61M 39/06* (2006.01)
*A61M 19/00* (2006.01)
(Continued)

(52) U.S. Cl.
CPC ........ *A61M 25/0662* (2013.01); *A61M 19/00* (2013.01); *A61M 2025/0006* (2013.01);
(Continued)

(58) Field of Classification Search
CPC ...... A61M 2039/0673; A61M 39/0613; A61M 2025/0006; A61M 25/013;
(Continued)

(56) References Cited

U.S. PATENT DOCUMENTS 4,857,062 A * 8/1989 Russell ............. A61M 39/0613 604/905
5,059,186 A * 10/1991 Yamamoto ......... A61M 25/0111 604/167.03
(Continued)

FOREIGN PATENT DOCUMENTS

DE 3242238 A1 5/1984
DE 3830653 C2 8/1990
(Continued)

OTHER PUBLICATIONS

B. Braun: Contiplex, D Cannula, Internet catalog, published before May 23, 2022, URL: https://www.bbraun.de/de/products/b1/contiplex-d-kanuele.html, with partial translation, 5 pages.
(Continued)

*Primary Examiner* — Emily L Schmidt
*Assistant Examiner* — Martin A Radomski
(74) *Attorney, Agent, or Firm* — Christopher A. Rothe; CM Law

(57) ABSTRACT

A catheter arrangement for use in peripheral regional anaesthesia includes a capillary with a capillary tube, a capillary attachment joined to the capillary tube, and a catheter hose which is pushed through the capillary attachment into the capillary tube. An end of the catheter hose protrudes from an end of the capillary tube by an axial length. A fixing device includes an actuation element and a clamping element mounted on the capillary attachment. The actuation element is mounted on the capillary attachment movably relative to the capillary attachment and operatively connected to the clamping element in a force-transmitting and/or movement-transmitting manner. The clamping element can be transferred between a clamping configuration, in which an axial mobility of the catheter hose is fixed, and an enabling
(Continued)

configuration, in which the action is cancelled and the axial mobility of the catheter hose is enabled.

15 Claims, 3 Drawing Sheets

(51) Int. Cl.

| | |
|---|---|
| ***A61M 25/06*** | (2006.01) |
| *A61M 25/00* | (2006.01) |
| *A61M 25/01* | (2006.01) |
| *A61M 25/09* | (2006.01) |
| *A61M 39/28* | (2006.01) |

(52) U.S. Cl.

CPC ... *A61M 25/013* (2013.01); *A61M 2025/0681* (2013.01); *A61M 2025/09116* (2013.01); *A61M 2025/09125* (2013.01); *A61M 39/0613* (2013.01); *A61M 2039/0673* (2013.01); *A61M 39/283* (2013.01)

(58) Field of Classification Search

CPC ...... A61M 2025/09116; A61M 39/283; A61M 2025/09125

See application file for complete search history.

(56) References Cited

U.S. PATENT DOCUMENTS

| | | | | |
|---|---|---|---|---|
| 5,106,376 A | | 4/1992 | Mononen et al. | |
| 5,269,764 A | * | 12/1993 | Vetter ............... | A61M 39/0613 604/167.04 |
| 5,389,079 A | | 2/1995 | Waskoenig | |
| 5,599,327 A | * | 2/1997 | Sugahara .......... | A61M 39/0613 604/539 |
| 5,935,112 A | * | 8/1999 | Stevens ............. | A61M 39/0613 604/246 |
| 9,486,193 B2 | * | 11/2016 | Vidlund ............. | A61B 17/0057 |
| 10,758,717 B2 | | 9/2020 | Gianotti et al. | |
| 2004/0087931 A1 | | 5/2004 | Marsh et al. | |
| 2007/0149949 A1 | | 6/2007 | Porter et al. | |
| 2010/0036329 A1 | * | 2/2010 | Razack ............. | A61M 39/0613 604/256 |
| 2012/0059308 A1 | | 3/2012 | Hsu et al. | |
| 2012/0143246 A1 | | 6/2012 | Zhu et al. | |
| 2013/0158427 A1 | | 6/2013 | Choi | |
| 2014/0025039 A1 | | 1/2014 | Rajendran et al. | |
| 2014/0276453 A1 | * | 9/2014 | Woehr ................ | A61M 5/3273 604/246 |
| 2018/0326197 A1 | * | 11/2018 | McArthur ....... | A61M 25/09041 |

FOREIGN PATENT DOCUMENTS

| | | | |
|---|---|---|---|
| DE | 4206347 | C1 | 12/1993 |
| DE | 29503750 | U | 4/1995 |
| DE | 295037504 | U1 | 4/1995 |
| DE | 102008025878 | A1 | 12/2009 |
| EP | 1002500 | A1 | 5/2000 |
| EP | 2226022 | A1 | 9/2010 |
| EP | 3909528 | A1 | 11/2021 |
| WO | 2020221381 | A1 | 11/2020 |

OTHER PUBLICATIONS

Pandurovic, Milan: “Blockade of the femoral nerve-a clinical comparison of the conventional technique with a modified technique using lateral cutaneal femoral nerve stimulation,” Apr. 19, 2006, https://oparu.uni-ulm.de/xmlui/handle/123456789/678, with translation of pages cited in a Search Report from a corresponding German application, 88 pages.

NonFinal Office Action received in U.S. Appl. No. 18/197,261 dated Dec. 23, 2025, 27 pages.

* cited by examiner

CATHETER ARRANGEMENT FOR USE IN PERIPHERAL REGIONAL ANAESTHESIA

CROSS-REFERENCE TO RELATED APPLICATION(S)

This application claims priority under 35 U.S.C. § 119 to German Application No. 10 2022 205 130.0, filed May 23, 2022, the content of which is incorporated by reference herein in its entirety.

FIELD

The disclosure relates to a catheter arrangement for use in peripheral regional anaesthesia, having a capillary with a capillary tube and a capillary attachment which is joined to a proximal tube end of the capillary tube, and a catheter hose which is pushed in the distal direction through the capillary attachment into the capillary tube, wherein a distal hose end of the catheter hose protrudes from a distal tube end of the capillary tube by an axial length.

BACKGROUND

Catheter arrangements of this kind are generally known in the field of regional anaesthesia and are used to block individual nerves in a targeted and reversible manner. This is also referred to as a nerve blockade or nerve block. The nerve blockade is brought about by administering an anaesthetic in direct proximity to the nerve in question. For this purpose, the known catheter arrangement has a capillary with a capillary tube and a capillary attachment, and also a catheter hose. The capillary can also be designated as a short catheter and is usually applied to the patient together with a cannula that is advanced distally through the capillary tube. After the cannula has been pulled back and removed, the capillary tube remains in the patient and serves to receive and guide the catheter hose. In order to reach the nerve that is to be blocked, the distal hose end is pushed through the capillary attachment in the distal direction into the capillary tube. In the known catheter arrangement, the axial length, i.e. the axial protrusion of the distal hose end beyond the distal tube end, is structurally defined. Therefore, the protrusion is always identical and unalterable.

SUMMARY

The object of the disclosure is to make available a catheter arrangement of the aforementioned type which permits improved regional anaesthesia.

This object is achieved by the fact that a fixing device with an actuation element and with a clamping element is present, wherein the clamping element is mounted on the capillary attachment, wherein the actuation element is mounted on the capillary attachment movably relative to the capillary attachment and is operatively connected to the clamping element in a force-transmitting and/or movement-transmitting manner, and wherein the clamping element, by means of a movement of the actuation element, can be transferred between a clamping configuration, in which an axial mobility of the catheter hose is fixed under the action of the clamping element, and an enabling configuration, in which the action is cancelled and the axial mobility of the catheter hose is enabled. By virtue of the solution according to the disclosure, the protrusion of the distal hose end can be adapted according to the particular situation and can be fixed after it has been adapted. This permits particularly precise positioning of the distal hose end. The anaesthetic to be dispensed from the distal hose end can in this way be applied particularly precisely to the nerve that is to be blocked. This permits improved analgesia. The fixing device that is present according to the disclosure permits said change of length and fixing of the catheter hose and for this purpose has said actuation element and said clamping element. The clamping element can be transferred between the clamping configuration and the enabling configuration, for example by means of a translational and/or rotational movement and/or deformation. The deformation can be elastic, plastic and/or elastoplastic. In the clamping configuration, the catheter hose is fixed under the action of the clamping element, more specifically held by frictional and/or form-fit engagement. In the enabling configuration, the action of the clamping element on the catheter hose is cancelled, such that the catheter hose can be advanced further in the distal direction and/or retracted in the proximal direction in order to allow the distal hose end to be positioned as precisely as possible. The clamping element is mounted at least indirectly on the capillary attachment. In one embodiment, the clamping element is mounted on a proximal end of the capillary attachment. In a further embodiment, the clamping element is alternatively or additionally received in a receiving recess of the capillary attachment, which receiving recess is open in particular in the proximal direction. The clamping element is mounted movably on the capillary attachment. In one embodiment, the actuation element is movable in rotation, in particular movable in a screwing motion. In a further embodiment, the actuation element is movable by pivoting. In a further embodiment, the actuation element is linearly movable. The movement and/or deformation of the clamping element between the clamping configuration and the enabling configuration is brought about by a manual actuation movement of the actuation element. For this purpose, the actuation element is operatively connected to the clamping element in a force-transmitting and/or movement-transmitting manner. In one embodiment, the operative connection is direct. In a further embodiment, the operative connection is indirect. In one embodiment, the clamping element and the actuation element are separate structural parts, in which case the operative connection can be effected by force-fit engagement, form-fit engagement and/or cohesive bonding. In a further embodiment, the actuation element is designed in one continuous piece with the clamping element and vice versa, such that said elements form different portions of a single structural part.

In one embodiment of the disclosure, the clamping element is pliable and has a lumen which is oriented coaxially with respect to the capillary tube and through which the catheter hose extends, wherein the clamping element, by means of the movement of the actuation element, is elastically deformable between the clamping configuration and the enabling configuration. In the clamping configuration, the lumen is radially narrowed by the elastic deformation, as a result of which the catheter hose is fixed by frictional engagement in the lumen. In the enabling configuration, the frictional engagement is cancelled. In this embodiment, the clamping element is elastically deformable between the clamping configuration and the enabling configuration. In the clamping configuration, the catheter hose is held, more specifically clamped, by frictional engagement in the lumen of the clamping element. In the enabling configuration, this clamping is cancelled, such that the catheter hose can be advanced further in the distal direction and/or retracted in the proximal direction in order to allow the distal hose end to be positioned as precisely as possible. In one embodiment, the dimensional conformability/elastic deformability is achieved by a suitable choice of material. For example, the clamping element can be produced from an elastomeric plastic material. In a further embodiment, the dimensional conformability/elastic deformability of the clamping element is achieved through its design; for example, the clamping element can be designed with a thin wall. The elastic deformation of the clamping element is brought about by a manual actuation movement of the actuation element.

In a further embodiment of the disclosure, the actuation element is mounted on the capillary attachment in such a way as to be axially movable by screwing and has a threaded portion which interacts with a complementary threaded portion of the capillary attachment. The threaded portion and the complementary threaded portion are thus oriented axially. The mounting of the actuation element with a screwing motion is easy to implement in design terms. Moreover, this allows ergonomically advantageous actuation. The forces and/or movements that are needed to move and/or deform the clamping element can be applied smoothly and particularly precisely by means of the actuation element mounted with a screwing motion.

In a further embodiment of the disclosure, the threaded portion is designed as an inner thread and the complementary threaded portion is designed as an outer thread. By such assigning of an inner thread and an outer thread to the different components of the catheter arrangement, simplified manufacture and assembly can be achieved in particular.

In a further embodiment of the disclosure, the actuation element has a collar portion which is oriented coaxially with respect to the lumen and engages in the circumferential direction around a proximal end of the capillary attachment. The collar portion permits an ergonomically advantageous actuation of the actuation element. If the actuation element has an inner thread in accordance with the preceding embodiment, the collar portion is preferably oriented coaxially with respect to the inner thread.

In a further embodiment of the disclosure, the clamping element is received in a proximally open receiving recess of the capillary attachment. The receiving recess is preferably oriented coaxially with respect to the capillary tube and/or the lumen. Axially compact dimensions of the capillary attachment can be achieved with this embodiment. This is in contrast to an embodiment in which the clamping element is mounted on a proximal end, in particular a proximal end face, of the capillary attachment.

In a further embodiment of the disclosure, the clamping element has an outer cone surface oriented coaxially with respect to the lumen and tapering in the distal direction, wherein, in the clamping configuration, the outer cone surface is pressed against an inner cone surface of the receiving recess. By means of the outer cone surface being pressed onto the inner cone surface, the clamping element is elastically deformed into the clamping configuration. The pressing movement brings about the radial narrowing of the lumen. The inner cone surface is at least in part complementary to the outer cone surface. In the enabling configuration, the outer cone surface is not pressed, or is pressed less strongly, against the inner cone surface. An actuation movement of the actuation element in this embodiment brings about a relative movement between the outer cone surface and the inner cone surface. In the case of an actuation in the direction of the clamping configuration, the outer cone surface is displaced distally relative to the inner cone surface. In the case of an actuation movement in the direction of the enabling configuration, the outer cone surface is displaced proximally relative to the inner cone surface.

In a further embodiment of the disclosure, the lumen extends between a proximal insertion opening with a first diameter and a distal outlet opening with a second diameter, wherein the first diameter is greater than the second diameter. The by comparison greater first diameter permits in particular a simplified insertion of the distal hose end into the lumen. The lumen preferably extends in a straight line. Preferably, the distal outlet opening is spaced apart proximally from the proximal tube end of the capillary tube.

In a further embodiment of the disclosure, the proximal insertion opening leads into a distally tapering inner cone of the lumen. The inner cone permits further simplified insertion of the catheter hose.

In a further embodiment of the disclosure, the actuation element is mounted on the clamping element in such a way as to be fixed axially by form—fit engagement and to be movable by sliding in the circumferential direction. The form-fit engagement acts at least in the distal direction. Preferably, the form-fit engagement acts axially in both directions, i.e. distally and proximally. In this embodiment, the actuation element and the clamping element are separately manufactured structural parts that are joined to each other, in this case by form-fit engagement.

In a further embodiment of the disclosure, the clamping element has a proximally arranged bearing portion with a slide surface oriented coaxially with respect to the lumen and with a run-on shoulder distally delimiting the slide surface, wherein the bearing portion engages axially through a bore of the actuation element oriented coaxially with respect to the lumen, and wherein an inner circumferential surface of the bore is supported slidably on the slide surface. This embodiment affords advantages in terms of design and function. The slide surface and the inner circumferential surface serve for the slidable mounting of the actuation element on the clamping element. The slide surface is preferably an outer circumferential surface. An internal diameter of the inner circumferential surface and an external diameter of the slide surface are preferably matched to each other in the manner of a clearance fit. The internal diameter is therefore slightly greater than the external diameter. The run-on shoulder serves for the axial form-fit engagement of the actuation element. In the case of an actuation movement in the direction of the clamping configuration, the actuation element presses in the distal direction onto the run-on shoulder. In one embodiment, the run-on shoulder is a radial flange extending all the way round in the circumferential direction. In a further embodiment, the run-on shoulder is formed by a plurality of radial projections arranged offset in the circumferential direction.

In a further embodiment of the disclosure, the clamping element is produced from an elastomeric plastic material, and/or the actuation element is produced from plastic material that is dimensionally stable compared to the clamping element. This choice of material helps give the clamping element the dimensional conformability/elastic deformability/pliable properties appropriate to the requirements.

BRIEF DESCRIPTION OF THE DRAWING FIGURES

Further advantages and features of the disclosure will become clear from the following description of a preferred exemplary embodiment of the disclosure which is shown in the drawings.

DETAILED DESCRIPTION

Figure 1:
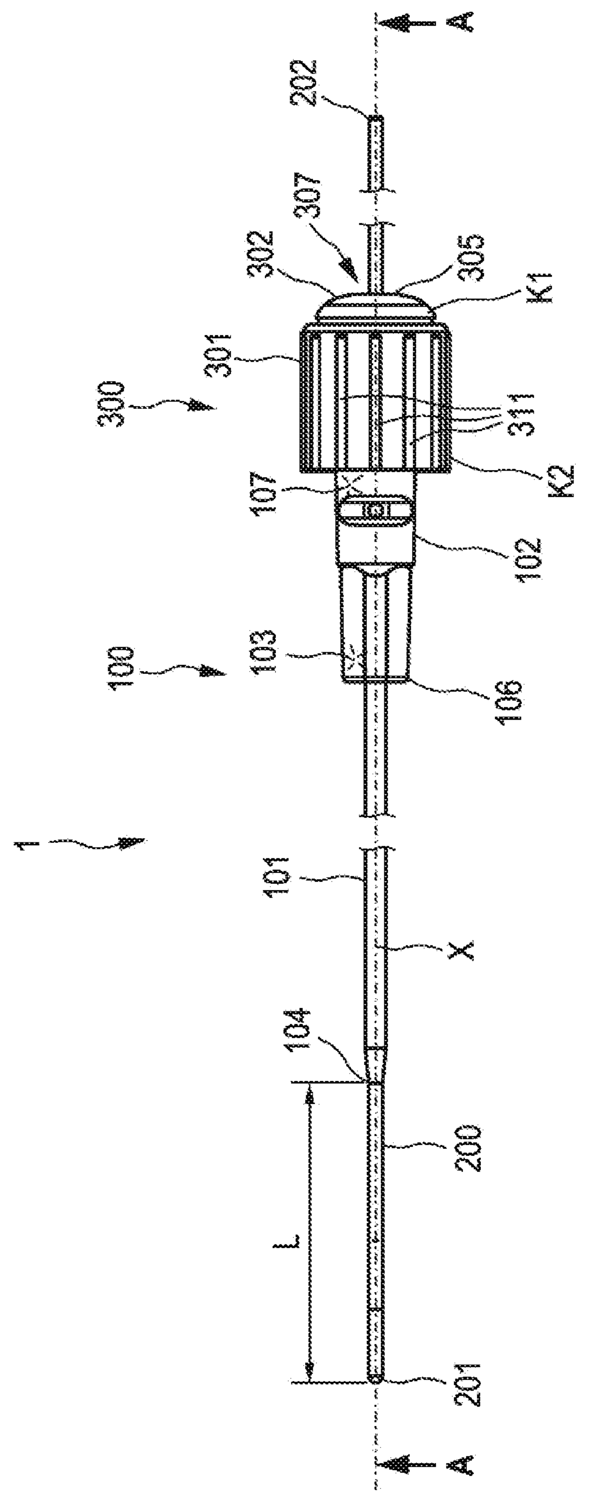
FIG. 1 shows a schematic side view of an embodiment of a catheter arrangement according to the disclosure with a capillary, a catheter hose and a fixing device.
Figure 2:
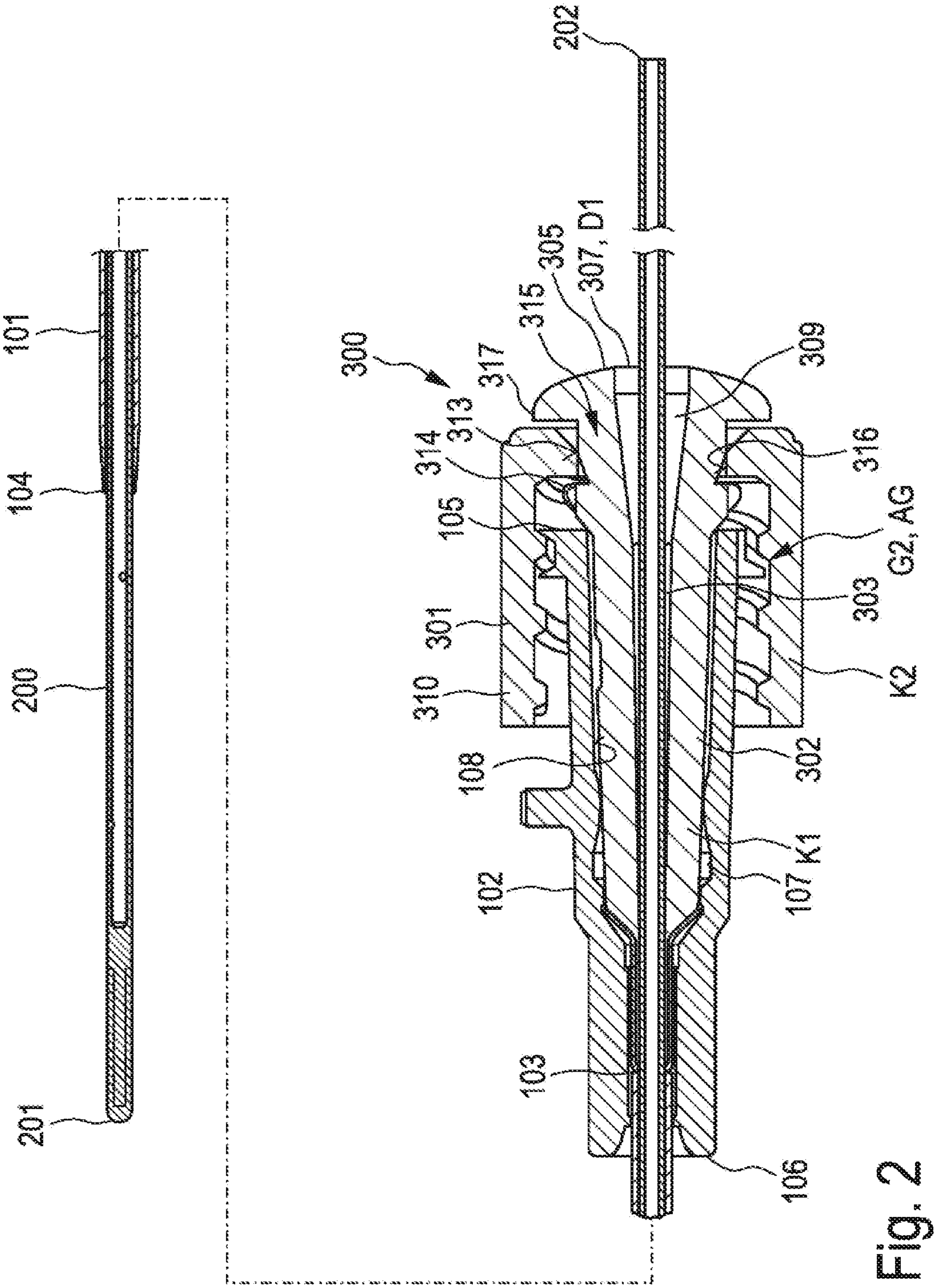
FIG. 2 shows the catheter arrangement according to FIG. 1 in a schematic, segmented longitudinal sectional view, along a section line A-A according to FIG. 1.

According to FIGS. 1 and 2, a catheter arrangement 1 for use in peripheral regional anaesthesia is provided.

The catheter arrangement 1 has a capillary 100, a catheter hose 200 and a fixing device 300.

The capillary 100 has a capillary tube 101 and a capillary attachment 102.

The capillary tube 101 can also be designated as a short catheter. The capillary tube 101 has a proximal tube end 103 and a distal tube end 104. The capillary tube 101 extends in a straight line between the proximal tube end 103 and the distal tube end 104.

The capillary attachment 102 is joined to the proximal tube end 103 (see FIG. 2). In the embodiment shown, a cohesively bonded join is provided. For example, the capillary attachment 102 can be welded and/or glued to the proximal tube end 103.

The catheter hose 200 extends between a distal hose end 201 and a proximal hose end 202. The catheter hose 200 is pushed in the distal direction through the capillary attachment 102 into the capillary tube 101, wherein the distal hose end 201 protrudes from the distal tube end 104 of the capillary tube 101 by an axial length L.

The axial length L (protrusion) is adaptable according to the situation and, after being adapted, can be fixed. The fixing device 300 is present for this purpose.

The fixing device 300 has an actuation element 301 and a clamping element 302.

The clamping element 302 is mounted on the capillary attachment 102. Details of the mounting are described in more detail below. Moreover, the clamping element 302 in the present case has a lumen 303. The lumen 303 (see FIG. 3) extends coaxially with respect to the capillary tube 101 and therefore also coaxially with respect to the catheter hose 200. The catheter hose 200 is received in the lumen 303 and/or extends through the latter (see FIG. 2).

The actuation element 301 is mounted on the capillary attachment 102 movably relative to the capillary attachment 102. Moreover, the actuation element 301 is connected to the clamping element 302 in a force-transmitting and/or movement-transmitting manner. As regards the embodiment shown, the specific implementation of the movable mounting and of the operative connection are described in more detail below.

In the embodiment shown, the clamping element 302 is dimensionally conformable, i.e. pliable. The clamping element 302, by means of a movement of the actuation element 301, is elastically deformable between a clamping configuration and an enabling configuration. In the clamping configuration, the clamping element 302 is elastically deformed in such a way that the lumen 303 is radially narrowed and the mobility of the catheter hose 200 is fixed by frictional engagement in the lumen 303. This clamping configuration is shown in FIGS. 1 and 2. In the enabling configuration, the frictional engagement between the lumen 303 and the catheter hose 200 is cancelled and the axial mobility of the catheter hose 200 relative to the lumen 303 and thus also to the capillary 100 is enabled.

In an embodiment not shown in the figures, the clamping element in the clamping configuration acts on the catheter hose in the manner of a cam. In said embodiment (not shown), the clamping element is not pliable and does not have a lumen.

The capillary tube 101, the capillary attachment 102, the catheter hose 200 and the lumen 303 are in the present case oriented coaxially with respect to a common longitudinal axis X.

Further structural and functional features of the embodiment shown are explained below. The explained features are advantageous, but they are not essential to the present disclosure.

In the embodiment shown, the capillary attachment 102 extends between a proximal end 105 and a distal end 106. The clamping element 302 and/or the actuation element 301 are mounted on the capillary attachment 102 in the region of the proximal end 105.

To mount the clamping element 302, the capillary attachment 102 has a receiving recess 107. The receiving recess 107 is open in the proximal direction. Starting from the proximal end 105, the receiving recess 107 extends in the distal direction into the capillary attachment 102. The capillary attachment and/or the receiving recess 107 has a proximal opening (not shown in detail) through which the clamping element 302 is inserted in the distal direction into the receiving recess 107. In the present case, the receiving recess 107 extends coaxially with respect to the lumen 303 and/or the capillary tube 101 and/or the catheter hose 200.

The receiving recess 107 has an inner cone surface 108. The inner cone surface 108 tapers in the distal direction. The inner cone surface 108 is in turn oriented coaxially. The inner cone surface 108 interacts with an at least partially complementary outer cone surface 304 of the clamping element 302. The outer cone surface 304 likewise tapers in the distal direction and, in the clamping configuration, is pressed onto the inner cone surface 108. As a result of this pressing movement, the clamping element 302 is elastically deformed and the lumen 303 narrows in the radial direction. This narrowing leads to (strengthened) frictional engagement with the catheter hose 200, such that the latter is clamped axially in the lumen 303 by friction.

Figure 3:
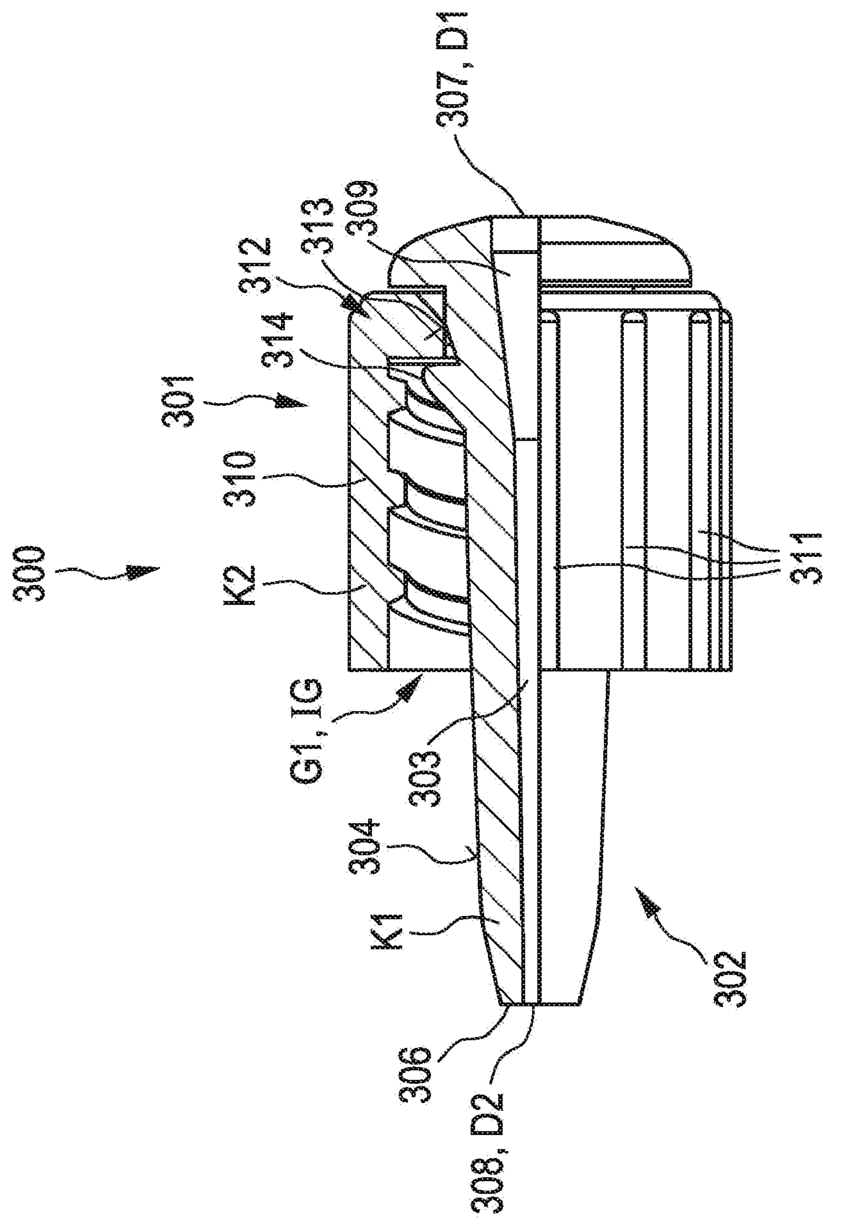
FIG. 3 shows the fixing device of the catheter arrangement according to FIGS. 1 and 2 in a partial longitudinal sectional view.

The clamping element 302 has a proximal end 305 and a distal end 306 (see FIG. 3). The outer cone surface 304 extends between the proximal end 305 and the distal end 306. In the embodiment shown, the proximal end 305 protrudes proximally from the receiving recess 107. The lumen 303 extends continuously between the proximal end 305 and the distal end 306 and has a proximal insertion opening 307 and a distal outlet opening 308. The proximal insertion opening 307 has a first diameter D1. The distal outlet opening 308 has a second diameter D2. The first diameter D1 is greater than the second diameter D2. The comparatively greater first diameter D1 facilitates the axial insertion of the catheter hose 200 into the lumen 303. Moreover, the proximal insertion opening 307 in the present case leads into a distally tapering inner cone 309 of the lumen 303. The inner cone 309 forms a lumen portion of the lumen 303. The inner cone 309 further facilitates insertion of the catheter hose 200.

In the embodiment shown, the actuation element 301 is mounted on the capillary attachment 102 in such a way as to be movable by screwing. In the case of a movement in the clockwise direction, the actuation element 301 is screwed distally onto the capillary attachment 102. As a result of said movement of the actuation element 301, the clamping element 302 operatively connected to the actuation element 301 is moved distally into the receiving recess 107. This leads to the above-explained interaction between the inner cone surface 108 and the outer cone surface 304, such that the lumen 303 is radially narrowed and the catheter hose 200 is clamped.

For mounting the actuation element 301 in such a way as to be movable by screwing, the actuation element 301 has a threaded portion G1. The threaded portion G1 interacts with a complementary threaded portion G2 of the capillary attachment 102. In the embodiment shown, the threaded portion G1 of the actuation element 301 is an inner thread IG. The complementary threaded portion G2 is accordingly an outer thread AG. The outer thread AG is arranged proximally on the capillary attachment 102. In the present case, the outer thread AG directly borders the proximal end 105 of the capillary attachment 102. Both threaded portions G1, G2 are oriented coaxially with respect to the lumen 303 and/or to the common longitudinal axis X.

In the embodiment shown, the actuation element 301 has a collar portion 310. The collar portion 310 is oriented coaxially with respect to the lumen 303 and engages in the circumferential direction around the proximal end 105 of the capillary attachment 102. The threaded portion G1, in the present case specifically the inner thread IG, is formed on an inner side (not shown in detail) of the collar portion 310. In the embodiment shown, the collar portion 310 has a plurality of radial projections 311 (see FIG. 1) arranged offset from one another in the circumferential direction. For rotational actuation, the actuation portion 301 is gripped between the fingers of one hand. The radial projections 311 counteract slipping of the fingers.

In the embodiment shown, the actuation element 301 is operatively connected to the clamping element 302 in such a way as to be fixed axially by form-fit engagement and to be movable by sliding in the circumferential direction.

In an embodiment not shown in the figures, the clamping element and the actuation element are fixedly connected to each other. In a further embodiment, an integral connection is provided between clamping element and actuation element, such that both elements form different portions of one and the same structural part.

To mount the actuation element 301 such that it is fixed axially by form-fit engagement and is movable by sliding in the circumferential direction, the clamping element 302 has a bearing portion 312. The bearing portion 312 is arranged proximally. The bearing portion 312 borders the proximal end 305. The bearing portion 312 has a slide surface 313 and a run-on shoulder 314.

The slide surface 313 is oriented coaxially with respect to the lumen 303 and/or the longitudinal axis X. The clamping element 302 engages through a bore 315 of the actuation element. The bore 315 has an inner circumferential surface 316. The inner circumferential surface 316 is received slidably on the slide surface 313. The bore 315 is oriented coaxially with respect to the lumen 303 and/or the longitudinal axis X. The same applies, mutatis mutandis, to the inner circumferential surface 316. The run-on shoulder 314 limits the distal relative mobility of the actuation element 301 with respect to the clamping element 302. In the case of a clockwise rotational actuation of the actuation element 301 in the direction of the clamping configuration, the actuation element 301, specifically an edge (not shown in detail) of the bore 315, comes to bear with form-fit engagement on the run-on shoulder 314. In the embodiment shown, the bearing portion 312 has a further run-on shoulder 317. The run-on shoulder 317 can also be designated as proximal run-on shoulder and limits the proximal relative mobility of the actuation element 301. Accordingly, the run-on shoulder 314 can also be designated as distal run-on shoulder. The actuation element 301 is held axially, in the region of the bore 315, by form-fit engagement between the two run-on shoulders 314, 317.

In the embodiment shown, the clamping element 302 is produced from an elastomeric plastic material K1. The actuation element is produced from a plastic material K2. The plastic material K2 is dimensionally stable compared to the elastomeric plastic material K1.

To transfer the fixing device 300 into the enabling configuration, starting from the clamping configuration shown in the figures, the actuation element 301 is actuated anticlockwise. In this way, the actuation element 301 is displaced in the proximal direction relative to the capillary attachment 102 by a screwing action. The inner circumferential surface 316 of the bore 315 slides in the circumferential direction on the slide surface 313 of the bearing portion 312 of the clamping element 302. At the same time, the actuation element 301 presses against the proximal run-on shoulder 317, such that the clamping element 302 together with the actuation element 301 is displaced in the proximal direction. Because of the proximal displacement, the operative connection between the outer cone surface of the clamping element 302 and the inner cone surface 108 is cancelled. The clamping element 302 is released elastically outwards in the radial direction. This leads to a radial expansion movement of the lumen 303. As a result of this expansion, the frictional engagement between the lumen 303 and the catheter hose 200 is cancelled or at least reduced. The cancelled or at least reduced frictional engagement enables the axial mobility of the catheter hose 200, such that the axial length L can be adapted according to the particular situation.

After the axial length L has been adapted, the catheter hose 200 can once again be fixed. For this purpose, the actuation element 301 is rotated clockwise. The inner circumferential surface 316 once again slides in the circumferential direction on the slide surface 313. The edge (not shown in detail) of the bore 315 comes to bear on the distal run-on shoulder 314 and thus presses the clamping element 302 into the receiving recess 107. In this way, the outer cone surface 304 is pressed onto the inner cone surface 108. The pressing action causes an elastic deformation of the clamping element 302 in such a way that the lumen 303 is narrowed in the radial direction. Because of the narrowing of the lumen 303, the catheter hose 200 is clamped and fixed in terms of its relative axial mobility.

The invention claimed is:

1. A catheter arrangement for use in peripheral regional anaesthesia, the catheter arrangement comprising:

a capillary with a capillary tube and a capillary attachment that is joined to a proximal tube end of the capillary tube;

a catheter hose that is pushed in a distal direction through the capillary attachment into the capillary tube, a distal hose end of the catheter hose protruding from a distal tube end of the capillary tube by an axial length; and a fixing device with an actuation element and a clamping element mounted on the capillary attachment, the actuation element being mounted on the capillary attachment movably relative to the capillary attachment and operatively connected to the clamping element in a force-transmitting and/or movement-transmitting manner, and the clamping element and the actuation element have therebetween a proximal engagement structure via which the clamping element is movable, by a movement of the actuation element in a proximal direction, from a clamping configuration, in which an axial mobility of the catheter hose is fixed under an action of the clamping element, to an enabling configuration, in which the action of the clamping element is cancelled and the axial mobility of the catheter hose is enabled, wherein the actuation element and the clamping element are independently rotatable about a longitudinal axis of the capillary attachment, wherein the proximal engagement structure comprises a proximally-facing surface formed on the actuation element and a proximal run-on shoulder formed on the clamping element at a location proximal to the proximally-facing surface, wherein the proximally-facing surface abuts and pushes against the proximal run-on shoulder when the actuation element is moved proximally to thereby move the clamping element from the clamping configuration to the enabling configuration.

2. The catheter arrangement according to claim 1, wherein the clamping element is dimensionally conformable and has a lumen which is oriented coaxially with respect to the capillary tube and through which the catheter hose extends, wherein the clamping element, by means of the movement of the actuation element, is elastically deformable in such a way that the lumen, in the clamping configuration, is radially narrowed by frictionally engaged fixing of the catheter hose, and the frictional engagement is cancelled in the enabling configuration.

3. The catheter arrangement according to claim 1, wherein the actuation element is mounted on the capillary attachment in such a way as to be axially movable by screwing and has a threaded portion which interacts with a complementary threaded portion of the capillary attachment.

4. The catheter arrangement according to claim 3, wherein the threaded portion is designed as an inner thread and the complementary threaded portion is designed as an outer thread.

5. The catheter arrangement according to claim 2, wherein the actuation element has a collar portion which is oriented coaxially with respect to the lumen and engages in a circumferential direction around a proximal end of the capillary attachment.

6. The catheter arrangement according to claim 2, wherein the clamping element has an outer cone surface oriented coaxially with respect to the lumen and tapering in the distal direction, wherein, in the clamping configuration, the outer cone surface is pressed against an inner cone surface of a receiving recess.

7. The catheter arrangement according to claim 2, wherein the lumen extends between a proximal insertion opening with a first diameter and a distal outlet opening with a second diameter, wherein the first diameter is greater than the second diameter.

8. The catheter arrangement according to claim 7, wherein the proximal insertion opening leads into a distally tapering inner cone of the lumen.

9. The catheter arrangement according to claim 1, wherein the clamping element is produced from an elastomeric plastic material and/or the actuation element is produced from a plastic material that is dimensionally stable compared to the clamping element.

10. The catheter arrangement according to claim 1, wherein the clamping element is received in a proximally open receiving recess of the capillary attachment.

11. The catheter arrangement according to claim 1, wherein the actuation element is mounted on the clamping element in such a way as to be fixed axially by form-fit engagement and to be movable by sliding in a circumferential direction.

12. The catheter arrangement of claim 1, wherein the clamping element and the actuation element have therebetween a distal engagement structure via which the clamping element is movable, by a movement of the actuation element in the distal direction, from the enabling configuration to the clamping configuration.

13. The catheter arrangement of claim 12, wherein the distal engagement structure comprises a distally-facing surface formed on the actuation element and a distal run-on shoulder formed on the clamping element at a location distal to the distally-facing surface, wherein the distally-facing surface abuts and pushes against distal proximal run-on shoulder when the actuation element is moved distally to thereby move the clamping element from the enabling configuration to the clamping configuration.

14. The catheter arrangement of claim 13, wherein the distally-facing surface and the proximally-facing surface are located on a bearing portion extending radially towards a lumen extending along a longitudinal axis of the clamping element.

15. A catheter arrangement for use in peripheral regional anaesthesia, the catheter arrangement comprising:

a capillary with a capillary tube and a capillary attachment that is joined to a proximal tube end of the capillary tube;

a catheter hose that is pushed in a distal direction through the capillary attachment into the capillary tube, a distal hose end of the catheter hose protruding from a distal tube end of the capillary tube by an axial length; and a fixing device with an actuation element and a clamping element mounted on the capillary attachment, the actuation element being mounted on the capillary attachment movably relative to the capillary attachment and operatively connected to the clamping element in a force-transmitting and/or movement-transmitting manner, and the clamping element and the actuation element have therebetween a proximal engagement structure via which the clamping element is movable, by a movement of the actuation element in a proximal direction, from a clamping configuration, in which an axial mobility of the catheter hose is fixed under an action of the clamping element, to an enabling configuration, in which the action of the clamping element is cancelled and the axial mobility of the catheter hose is enabled, wherein the actuation element and the clamping element are independently rotatable about a longitudinal axis of the capillary attachment, wherein the clamping element is dimensionally conformable and has a lumen which is oriented coaxially with respect to the capillary tube and through which the catheter hose extends, wherein the clamping element, by means of the movement of the actuation element, is elastically deformable in such a way that the lumen, in the clamping configuration, is radially narrowed by frictionally engaged fixing of the catheter hose, and the frictional engagement is cancelled in the enabling configuration, wherein the clamping element has a proximally arranged bearing portion with a slide surface oriented coaxially with respect to the lumen and with a run-on shoulder distally delimiting the slide surface, wherein the proximally arranged bearing portion engages axially through a bore of the actuation element oriented coaxially with respect to the lumen, and wherein an inner circumferential surface of the bore is supported slidably on the slide surface.

* * * * *